(12) United States Patent
Cazalis et al.

(10) Patent No.: US 9,110,079 B2
(45) Date of Patent: Aug. 18, 2015

(54) METHOD AND KIT FOR ESTABLISHING AN IN VITRO PROGNOSIS ON A PATIENT EXHIBITING SIRS

(75) Inventors: Marie-Angélique Cazalis, Velin (FR); Alexandre Pachot, Sulignat (FR); Sylvie Tissot, Lyons (FR); Guillaume Monneret, Lyons (FR)

(73) Assignees: BIOMERIEUX, Marcy L'Etoile (FR); HOSPICES CIVILS DE LYON (HCL), Lyons (FR)

( * ) Notice: Subject to any disclaimer, the term of this patent is extended or adjusted under 35 U.S.C. 154(b) by 370 days.

(21) Appl. No.: 13/242,412

(22) Filed: Sep. 23, 2011

(65) Prior Publication Data

US 2012/0077693 A1  Mar. 29, 2012

Related U.S. Application Data

(60) Provisional application No. 61/387,536, filed on Sep. 29, 2010.

(51) Int. Cl.
*C12Q 1/68* (2006.01)
*G01N 33/68* (2006.01)

(52) U.S. Cl.
CPC .......... *G01N 33/6863* (2013.01); *C12Q 1/6883* (2013.01); *C12Q 2600/118* (2013.01); *C12Q 2600/158* (2013.01); *G01N 2333/7158* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| | | | |
|---|---|---|---|
| 4,672,040 | A | 6/1987 | Josephson |
| 4,683,195 | A | 7/1987 | Mullis et al. |
| 4,683,202 | A | 7/1987 | Mullis et al. |
| 4,800,159 | A | 1/1989 | Mullis et al. |
| 4,981,783 | A | 1/1991 | Augenlicht |
| 5,399,491 | A | 3/1995 | Kacian et al. |
| 5,445,934 | A | 8/1995 | Fodor et al. |
| 5,700,637 | A | 12/1997 | Southern |
| 5,744,305 | A | 4/1998 | Fodor et al. |
| 5,750,338 | A | 5/1998 | Collins et al. |
| 5,807,522 | A | 9/1998 | Brown et al. |
| 6,376,179 | B1 | 4/2002 | Laayoun |

FOREIGN PATENT DOCUMENTS

| | | |
|---|---|---|
| EP | 0 201 184 A2 | 12/1986 |
| FR | 0 014 896 | 10/1911 |
| FR | 14691 E | 12/1911 |
| FR | 2 780 059 A1 | 12/1999 |
| WO | WO 89/10977 A1 | 11/1989 |
| WO | WO 90/01069 A1 | 2/1990 |
| WO | WO 90/03382 A1 | 4/1990 |
| WO | WO 90/06995 A1 | 6/1990 |
| WO | WO 91/02818 A1 | 3/1991 |
| WO | WO 91/19812 | 12/1991 |
| WO | WO 91/19812 A1 | 12/1991 |
| WO | WO 94/12670 A2 | 6/1994 |
| WO | WO 95/08000 A2 | 3/1995 |
| WO | WO 97/45202 A1 | 12/1997 |
| WO | WO 99/35500 A1 | 7/1999 |
| WO | WO 99/65926 A1 | 12/1999 |
| WO | WO 00/71750 A1 | 11/2000 |
| WO | WO 01/44506 A1 | 6/2001 |
| WO | WO 01/44507 A1 | 6/2001 |
| WO | WO 02/090319 | 11/2002 |
| WO | WO 02/090584 A2 | 11/2002 |

OTHER PUBLICATIONS

Levy et al., "2001 SCCM/ESICM/ACCP/ATS/SIS International Sepsis Definitions Conference," Crit Care Med 2003, pp. 1250-1256, vol. 31, No. 4.
Boom et al., "Rapid and Simple method for Purification of Nucleic Acids," Journal of Clinical Microbiology, Mar. 1990, pp. 495-503.
Levison et al., "New approaches to the isolation of DNA by ion-exchange chromatography," Journal of Chromatography A. 827 (1998), pp. 337-344.
Nielsen et al., "Sequence-Selective Recognition of DNA by Strand Displacement with a Thymine-Substituted Polyamide," Dec. 6, 1991, Science, vol. 254, pp. 1497-1500.
Kricka, Larry J., "Nucleic Acid Detection Technologies—Labels, Strategies, and Formats," Clinical Chemistry, (1999) pp. 453-458.
Keller, George H., "Non-Radioactive Labeling Procedures," DNA Probes, $2^{nd}$ Edition, (1993) pp. 173-253.
Tyagi et al., "Molecular Beacons: Probes that Fluoresce upon Hybridization," Nature Biotechnology, vol. 14 Mar. 1996, pp. 303-308.
Chee et al., "Accessing Genetic Information with High-Density DNA Arrays," Science vol. 274, Oct. 25, 1996, pp. 610-614.
Caviani et al., "Light-generated oligonucleotide arrays for rapid DNA sequence analysis," Proc. Natl. Acad. Science USA May 1994, vol. 91. pp. 5022-5026.
Ramsay, Graham, "DNA chips: State-of-the art," Nature Biotechnology vol. 16 Jan. 1998, pp. 40-44.
Ginot, Frederic, "Oligonucleotide Micro-Arrays for Identification of Unknown Mutations,": How Far from Reality? Human Mutation 10:1-10 (1997) Wiley-liss, Inc.
Livache et al., "Preparation of a DNA matrix via an electrochemically directed copolymerization of pyrrole and oligonucleotides bearing a pyrrole group," Nucleic Acids Research, 1994, vol. 22, No. 15 pp. 2915-2921.
Cheng et al., "Preparation and hybridization analysis of DNA/RNA from *E. coli* on microfabricated bioelectronic chips," Nature Biotechnology vol. 16 Jun. 1998, pp. 541-546.

(Continued)

*Primary Examiner* — Jim Ketter
(74) *Attorney, Agent, or Firm* — Oliff PLC

(57) ABSTRACT

A method and a kit for establishing an in vitro prognosis on a patient exhibiting SIRS, the method comprising: (i) measuring the level of expression of the CX3CR1 gene in vitro from the biological material of a patient sample by bringing into contact said sample with a specific reagent of the CX3CR1 gene; and (ii) comparing the expression level of the CX3CR1 gene of the patient to a predetermined expression threshold; wherein (iii) if the expression level of the CX3CR1 gene of the patient is less than the predetermined expression threshold, the survival prognosis of the patient is poor, and if the expression level of the CX3CR1 gene of the patient is greater than the predetermined expression threshold, the survival prognosis of the patient is good.

27 Claims, 3 Drawing Sheets

(56) References Cited

OTHER PUBLICATIONS

Bustin, S A, "Quantification of mRNA using real-time reverse transcription PCR (RT-PCR): trends and problems," Journal of Molecular Endocrinology (2002) 29, pp. 23-39.

Giulietti et al., "An Overview of Real-Time Quantitative PCR: Applications to Quantify Cytokine Gene Expression," Methods 25, (2001) pp. 386-401.

Tobiasen et al., "The Abbreviated Burn Severity Index," Annals of Emergency Medicine, 1982, pp. 260-262.

Cheng, J. et al, "Microchip-based Devices for Molecular Diagnosis of Genetic Diseases," Molecular Diagnosis, pp. 183-200, vol. 1, No. 3, 1996.

Le Quang, Diane, "Etude de l'expression genomique chez le brule grave," pp. 47, 77, 78, 87, 88 and 96 (with partial English-language translation of the same), presented to Universite Claude Bernard-Lyon I and made public Sep. 30, 2009.

METHOD AND KIT FOR ESTABLISHING AN IN VITRO PROGNOSIS ON A PATIENT EXHIBITING SIRS

This is a non-provisional application of Provisional Application No. 61/387,536, filed on Sep. 29, 2010, which is hereby incorporated by reference.

TECHNICAL FIELD

The present invention relates to a method and a kit for establishing an in vitro prognosis on a patient exhibiting SIRS.

BACKGROUND

SIRS (Systemic Inflammatory Response Syndrome) is a systemic inflammatory response triggered by a variety of causes, infectious or not. When the SIRS is triggered by infectious causes, it is considered to be a SEPSIS. Among the states of SIRS triggered by non-infectious causes, mention may be made of all the stress factors which cause a systemic inflammatory response such as, for example, traumatic states, burns, pancreatitises, acute respiratory syndromes, major surgeries accompanied, or not, with cardiopulmonary bypass. The systemic inflammatory response manifests itself with at least two of the following signs: a) temperature above 38° C. or below 36° C.; b) heart rate above 90 beats per minute; c) breathing rate above 20 breaths per minute; d) leukocyte count above $12000/mm^3$ or below $4000/mm^3$, according to the defining criteria established by a group of experts in 2001 (M. M. Levy, M. P. Fink, J. C. Marshall, E. Abraham, D. Angus, D. Cook, J. Cohen, S. M. Opal, J. L. Vincent and G. Ramsay, 2001 SCCM/ESICM/ACCP/ATS/SIS International Sepsis Definitions Conference, *Crit. Care Med.* 31 (2003), pp. 1250-1256). Furthermore, the state of the patient presenting with SIRS is often made more complicated due to dysfunctions of one or several organs, and mostly because of an infectious complication which may be due to a pathogenic endogenous reactivation and/or nosocomial infections which can evolve toward an acute septic syndrome (SEPSIS, acute SEPSIS, septic shock). For all the reasons described above, SIRS patients present an increased risk of mortality, whereby death can occur at different stages of evolution of the SIRS. It is therefore necessary for the clinician to have available to him elements which enable him to determine whether the patient has a good or poor prognosis of survival. Indeed, identifying patient presenting high risks of mortality very early on after the beginning of a SIRS would enable the clinician to improve the success of a targeted and early care in intensive care by attributing adapted hospital resources and providing support to end-of-life medical decisions. Furthermore, identifying patients presenting a low risk of mortality could enable a clinician to anticipate their checking out of the intensive care unit to direct them toward a more suitable department, which is not negligible from an economic standpoint in terms of health management.

SUMMARY

We have shown that the expression level of the Fractalkine receptor, called CX3CR1 (chemokine (C-X3-C motif) receptor 1) of CX3CR1 is diminished in SIRS patients with respect to the normal population with a quantitative and differential analysis. Furthermore, we have found that CX3CR1 is an early label of mortality with patients presenting with SIRS. The CX3CR1 gene is referenced in GenBank under the accession number NM_001337.3, NM_001171174.1, NM_001171171.1, NM_001171172.1. Since there exists several variants of the gene CX3CR1, it is obvious that these different isoforms of the CX3CR1 gene, or even others, are relevant and are part of the invention such as claimed.

Thus, in embodiments, a method for establishing an in vitro prognosis on a patient exhibiting SIRS comprises the following steps:

(i) the level of expression of at least one CX3CR1 gene is measured in vitro from the biological material of a patient sample by bringing into contact said sample with at least one specific reagent of said at least one CX3CR1 gene, (ii) the expression level of said at least one CX3CR1 gene of the patient is compared to a predetermined expression threshold, and (iii) if the expression level of the CX3CR1 gene of the patient is inferior to the predetermined expression threshold, it is established that the survival prognosis of the patient is poor, and if the expression level of the CX3CR1 gene of the patient is greater than the predetermined expression threshold, it is established that the survival prognosis of the patient is good.

The predetermined expression threshold to be taken into consideration to carry out the method described above is determined by measuring the expression level of CX3CR1 in a representative cohort of individuals exhibiting SIRS. This threshold is calculated to achieve the best prediction for the risk of death in terms of sensitivity and specificity. It is possible for one having ordinary skill in the art to establish this predetermined expression threshold by means of known methods, as a function, for example, of studied populations (more or less important cohort), type of SIRS or of any other parameter in relation with the patient (age of patients, sex, associated treatment, etc.).

The sample described above is chosen among the group consisting of blood, serum, plasma, saliva, urine, cerebrospinal fluid, pleural fluid, peritoneal fluid, tissues, circulating cells. The biological sample comprises a biological material such as defined below. This biological material may be extracted, but not necessarily, from the biological sample by any technique known to one having ordinary skill in the art as described in detail below.

The biological material is, for example, a nucleic acid or a mixture of nucleic acids, a protein, or a mixture of proteins, so that in the steps (i) and (ii) described hereinabove, the specific reagent comprises:

at least one DNA probe, it being understood that, by DNA probe, one means any polynucleotide or nucleotide fragment which is capable of hybridizing to RNA or to DNA, under determined conditions of stringency, that is, a capture probe, a detection probe, a primer, or at least one monoclonal antibody, one polyclonal antibody, one humanized antibody, one human antibody, or one fragment of said antibodies, in particular fragments Fab, Fab', F(ab')2, ScFv, Fv, Fd.

In an embodiment of the invention, the biological sample of the patient in step (i) was collected at day 1, day 2, day 3, after the burn, which makes it possible to establish a very early prognosis.

In a preferred embodiment of the invention, the at least specific reagent of the gene CX3CR1 comprises at least:
one hybridization probe, or
one capture probe and one primer which is specific to the gene CX3CR1, or
one hybridization probe and two specific primers of the gene CX3CR1, or one antibody.

In a preferred embodiment, the expression level of at least one gene CX3CR1 in the patient sample and the expression level of at least one other target gene, different from CX3CR1, said at least other target gene being chosen among S100A8, S100A9, IL-10, TNFA, HLA-DR, CIITA and IRAK3, with at least one specific reagent of at least one of said other genes; said specific reagent preferably responding to other definitions given hereinabove.

The genes hereinabove are referenced in GenBank as follows:
S100A8: accession number NM_002964
S100A9: accession number NM_002965
IL10: accession number NM_000572
TNFA: accession number NM_000594
HLA-DR: accession number NM_019111
CIITA: accession number NM_000246
IRAK3: accession numbers NM_007199 and NM_001142523.

There sometimes are several variants for the same target gene, such as, for example, for IRAK-3 which has 2 isoforms. It is therefore obvious that if there are different isoforms of the other genes, all the isoforms are relevant and are part of the invention such as claimed.

The invention is also directed to a kit for establishing an in vitro prognosis on a patient exhibiting SIRS which comprises at least one specific reagent of at least one gene CX3CR1 and at least one specific reagent with at least one target gene chosen among S100A8, S100A9, IL-10, TNFA, HLA-DR, CIITA, IRAK3, under the condition that the kit comprises no more than 12 specific reagents of 12 target genes and instructions describing the predictive value of the expression of said genes to establish a good or poor survival prognosis for a SIRS patient.

Preferably, the kit comprises at least the specific reagent of at least one gene CX3CR1 and at least 2, 3, 4, 5, 6, 7, 8 specific reagents, respectively, of at least 2, 3, 4, 5, 6, 7, 8 target genes chosen among S100A8, S100A9, IL-10, TNFA, HLA-DR, CIITA, IRAK3, under the condition that the kit comprises no more than 12 specific reagents of 12 target genes and instructions describing the predictive value of the expression of said genes to establish a good or poor survival prognosis for a SIRS patient.

Finally, in an embodiment, the kit comprises at most 12 reagents which are specific reagents, respectively, of target genes CX3CR1, S100A8, S100A9, IL-10 TNFA, HLA-DR, CIITA, and IRAK3 and the instructions describing the predictive value of the expression of said genes to establish a good or poor survival prognosis for a SIRS patient.

The specific reagent or reagents preferably respond to the definitions given hereinabove in the prognosis method.

DETAILED DESCRIPTION OF EMBODIMENTS

Definitions

"Biological sample" signifies any sample taken from a patient or individual and susceptible to contain biological material such as defined hereinafter. This biological sample may, in particular, be a sample of blood, serum, plasma, saliva, urine, cerebrospinal fluid, pleural fluid, peritoneal fluid, tissues, circulating cells of the patient or of an individual. This biological sample is provided by any type of sample-taking known to one having ordinary skill in the art. It is, preferably, a blood sample.

The term "biological material" is intended to mean any material that makes it possible to detect the expression of a target gene. The biological material may comprise, in particular, proteins and/or nucleic acids such as, in particular, deoxyribonucleic acids (DNA) or ribonucleic acids (RNA). The biological material preferably comprises RNAs, and even more preferably, total RNAs. The total RNAs comprise transfer RNAs, messenger RNAs (mRNA), such as mRNAs transcribed from the target gene, but also transcribed from any other gene, and ribosomal RNAs. This biological material comprises material specific for a target gene, such as, in particular, the mRNAs transcribed from the target gene and/or the proteins derived from these mRNAs, but may also comprise material not specific for a target gene, such as, mRNAs transcribed from a gene other than the target gene, the tRNAs, the rRNAs derived from genes other than the target gene.

By way of example, when necessary, the extraction of nucleic acids or of proteins may be carried out by lysing the cells present in the biological sample in order to release the nucleic acids contained in the patient's cells. These lysis techniques are part of the general knowledge of one having ordinary skill in the art. By way of example, one can cite mixed magnetic and mechanical lysis, electric lysis, mechanical lysis, and other lysis methods, such as thermal or osmotic shocks or chemical lysis using chaotropic agents such as guanidium salts.

It is possible to also carry out, if desired, a purification step for separating the nucleic acids from the other cell constituents released in the lysis step or the separation of proteins from other cell constituents. When nucleic acids are concerned, this step generally makes it possible to concentrate the nucleic acids, and may be adapted to the purification of DNA or RNA. By way of example, use may be made of magnetic particles optionally coated with oligonucleotides, by adsorption or covalence (in this respect, see U.S. Pat. No. 4,672,040 and U.S. Pat. No. 5,750,338), and the nucleic acids which are bound to these magnetic particles may be purified by means of a washing step. This nucleic acid purification step is particularly advantageous if it is desired to subsequently amplify said nucleic acids. A particularly advantageous embodiment of these magnetic particles is described in patent applications WO-A-97/45202 and WO-A-99/35500. Another advantageous example of a nucleic acid purification method is the use of silica, either in the form of a column, or in the form of inert particles (Boom R. et al., J. Clin. Microbiol., 1990, n°28(3), p. 495-503) or magnetic particles (Merck: MagPrep Silica, Promega: MAGNESIL™ Paramagnetic particles). Other widely used methods are based on ion exchange resins in a column or in a paramagnetic particulate format (Whatman: DEAE-Magarose) (Levison P R et al., J. Chromatography, 1998, p. 337-344). Another method that is very relevant, but not exclusive, for an embodiment of the invention is that of the adsorption onto a metal oxide support (société Xtrana: matrice XTRA-BIND™).

To specifically extract DNA from a biological sample, an extraction may be carried out by means of phenol, chloroform and alcohol to eliminate the proteins and precipitate the DNA with 100% ethanol. The DNA can then be pelleted by centrifugation, washed, and put back into a solution.

To specifically extract RNAs from a biological sample, an extraction may be carried out by means of phenol, chloroform and alcohol to eliminate the proteins and precipitate the RNAs with 100% ethanol. The RNAs can then be pelleted by centrifugation, washed, and put back into a solution.

When the biological material comprises nucleic acids, they may be detected by hybridization with at least one hybridization probe (capture probe, detection probe, primer) which responds to the definitions given below. The term "hybridization" is intended to mean the process during which, under suitable conditions, two nucleotide fragments bind to one another with specific and stable hydrogen bonds, so as to form a double-stranded complex. These hydrogen bonds form between the complementary bases adenine (A) and thymine (T) (or uracil (U)) (this is described as an A-T bond) or between the complementary bases guanine (G) and cytosine (C) (this is described as a G-C bond). The hybridization of two nucleotide fragments may be complete (reference is then made to nucleotide fragments or complementary sequences), which means that the double-stranded complex obtained during this hybridization comprises only A-T bonds and C-G bonds. This hybridization may be partial (reference is then made to sufficiently complementary sequences or nucleotide fragments), which means that the doubled-stranded complex obtained comprises A-T bonds and C-G bonds that make it possible to form the double-stranded complex, but also bases that are not bound to a complementary base. The hybridization between two nucleotide fragments depends on the operating conditions that are used, and in particular on the stringency. The stringency is defined in particular according to the base composition of the two nucleotide fragments, and also by the degree of mismatching between two nucleotide fragments. The stringency may also depend on the reaction parameters, such as the concentration and the type of ionic species present in the hybridization solution, the nature and the concentration of denaturing agents and/or the hybridization temperature. All these data are well known and the appropriate conditions may be determined by one having ordinary skill in the art. In general, depending on the length of the nucleotide fragments that is desired to be hybridized, the hybridization temperature is comprised between approximately 20 and 70° C., in particular between 35 and 65° C. in a saline solution at a concentration of about 0.5 to 1 M. A sequence, or a nucleotide or oligonucleotide or polynucleotide fragment, is a series of nucleotide motifs assembled together via phosphoric ester bonds, characterized by the informational sequence of the natural nucleic acids capable of hybridizing to a nucleotide fragment, it being possible for the series to contain monomers with different structures and to be obtained from a natural nucleic acid molecule and/or by genetic recombination and/or by chemical synthesis. A motif is derived from a monomer which may be a natural nucleotide of nucleic acid, the constitutive elements of which are a sugar, a phosphate group, and a nitrogenous base: in DNA, the sugar is deoxy-2-ribose, in RNA, the sugar is ribose; depending on whether DNA or RNA is involved, the nitrogenous base is chosen among adenine, guanine, uracil, cytosine, thymine; alternatively, the monomer is a nucleotide, modified in one at least of three constitutive elements; by way of example, the modification may occur either at the level of the bases, with modified bases such as inosine, methyl-5deoxycytidine, deoxyuridine, dimethylamino-5 deoxyuridine, diamino-2,6-purine, bromo-5-deoxyuridine or any other modified base capable of hybridization, either at the level of the sugar, for example the replacement of at least one deoxyribose with a polyamide (P. E. Nielsen et al, Science, 254, 1497-1500 (1991), or else at the level of the phosphate group, for example replacement of the latter by esters chosen in particular from diphosphates, alkyl phosphonates, aryl phosphonates and phosphorothioates.

The term "hybridization probe" is intended to mean a nucleotide fragment comprising at least 5 nucleotides, such as from 5 to 100 nucleotides, in particular from 10 to 75 nucleotides, such as 15-35 nucleotides and 60-70 nucleotides, having a hybridization specificity under given conditions so as to form a hybridization complex with the material specific for the target gene. In an embodiment of the invention, the material specific for the target gene may be a nucleotide sequence comprised in an RNA messenger derived from the target gene (reference is then made to a target-gene-specific mRNA), a nucleotide sequence comprised in a complementary DNA obtained by reverse transcription of said RNA messenger (reference is then made to a target-gene-specific cDNA), or a nucleotide sequence comprised in a complementary RNA obtained by transcription of said cDNA such as previously described (reference is then made to target-gene-specific cRNA). The hybridization probe may comprise a label for its detection. The term "detection" encompasses the direct detection by a physical method and the indirect detection by a detection method using a label. Numerous methods of detection exist for detecting nucleic acids. [See, for example, Kricka et al., Clinical Chemistry, 1999, n° 45(4), p. 453-458 or Keller G. H. et al., DNA Probes, 2nd Ed., Stockton Press, 1993, sections 5 and 6, p. 173-249]. The term "label" is intended to mean a tracer capable of engendering a signal that can be detected. A non-limiting list of these tracers comprises enzymes which produce a signal, detectable, for example, by colorimetry, fluorescence, or luminescence, such as horseradish peroxidase, alkaline phosphatase, beta-galactosidase, glucose-6-phosphate dehydrogenase; chromophores such as fluorescent, luminescent, or dye compounds; the electron dense groups, detectable by electron microscopy or by virtue of their electrical properties such as conductivity, by amperometry or voltammetry methods, or by impedance measurements; groups that can be detected by optical methods such as diffraction, surface plasmon resonance, contact angle variation or by physical methods such as atomic force spectroscopy, tunnel effect, etc.; radioactive molecules such as $^{32}$P, $^{35}$S or $^{125}$I.

The hybridization probe may be a probe referred to as a "detection probe". In this case, the detection probe is labeled by means of a label such as defined above. The detection probe can, in particular, be a "molecular beacon" detection probe, such as described by Tyagi & Kramer (Nature biotech, 1996, 14:303-308). These "molecular beacons" become fluorescent during hybridization. They have a hairpin structure and contain a fluorophore and a "quencher" group. The binding of the specific loop sequence with its complementary target nucleic acid sequence causes the stem to unfold and a fluorescent signal to be emitted during excitation at the appropriate wavelength. It may be a "reporter probe" comprising a "color-coded barcode" according to the technology of de NANOSTRING™. For the detection of the hybridization reaction, use may be made of target sequences that have been labeled, directly (particularly by the incorporation of a label within the target sequence) or indirectly, (particularly using a detection probe such as defined above the target sequence). It is in particular possible to carry out, before the hybridization step, a step consisting in labeling and/or cleaving the target sequence, for example using a labeled deoxyribonucleotide triphosphate during the enzymatic amplification reaction. The cleavage may be carried out in particular by the action of imidazole and manganese chloride. The target sequence may also be labeled after the amplification step, for example by hybridizing a detection probe according to the sandwich hybridization technique described in document WO 91/19812. Another preferred method of labeling nucleic acids is described in application FR 2 780 059. According to an embodiment of the invention, the detection probe comprises a fluorophore and a quencher. According to another embodiment of the invention, the hybridization probe comprises an FAM (6-carboxy-fluorescein) or ROX (6-carboxy-X-rhodamine) fluorophore at its end 5' and a quencher (Dabsyl) at its end 3'.

The hybridization probe may also be a probe referred to as a "capture probe". In this case, the capture probe is immobilized or can be immobilized on a solid support by any appropriate means, i.e. directly or indirectly, for example by covalence or adsorption. As solid support, use may be made of synthetic materials or natural materials, optionally chemically modified, particularly polysaccharides such as cellulose-based materials, for example paper, cellulose derivatives such as cellulose acetate and nitrocellulose or dextran, polymers, copolymers, particularly based on styrene-type monomers, natural fibers such as cotton, and synthetic fibers such as nylon; inorganic materials such as silica, quartz, glass, or ceramics; latexes; magnetic particles, metal derivatives, gels, etc. The solid support may be in the form of a microtiter plate, of a membrane as described in application WO-A-94/12670, or of a particle. Several different capture probes, each being specific to a target gene, can also be immobilized on the support. In particular, a biochip on which a large number of probes can be immobilized may be used as support. The term "Biochip" is intended to mean a reduced-size solid support onto which a multitude of capture probes are attached at predetermined positions. The concept of a biochip, or DNA chip, dates back to the early nineties. It is based on a multi-disciplinary technology integrating micro-electronics, nucleic acid chemistry, image analysis, and computing. The operation principle is based on an underpinning of molecular biology: the hybridization phenomenon, that is, the pairing, by complementarity, of the bases of two DNA and/or RNA sequences. The biochips method is based on the use of capture probes attached to a solid support onto which a sample of target nucleotide fragments labeled directly or indirectly with fluorochromes is made to react. The capture probes are positioned specifically on the support or chip and each hybridization provides a particular item of information in relation with the target nucleotide fragment. The information obtained are cumulative and allow, for example, for quantifying the expression level of a gene or of several target genes. To analyze the expression of a target gene, a support, transcribed into mRNAs and comprising a multitude of probes that correspond to all or part of the target gene may be carried out. In embodiments, average density support relates to a support comprising from 50 to 10,000 probes. In embodiments, high density support relates to a support comprising more than 10,000 probes.

Then, for example, specific cDNA or cRNA of a target gene to be analyzed on specific capture probes are hybridized. After hybridization, the support or chip is washed, and the labeled cDNA or cRNA complexes/capture probes are revealed with a high-affinity ligand bonded, for example, to a fluorochrome-type label. The fluorescence is read by a scanner, for example, and the analysis of the fluorescence is performed by computing. By way of example, one can mention the DNA chips developed by the company Affymetrix ("Accessing Genetic Information with High-Density DNA arrays", M. Chee et al., Science, 1996, 274, 610-614. "Light-generated oligonucleotide arrays for rapide DNA sequence analysis", A. Caviani Pease et al., Proc. Natl. Acad. Sci. USA, 1994, 91, 5022-5026) for molecular diagnoses. With this technology, the capture probes generally have a reduced size, on the order of 25 nucleotides. Other examples of biochips are given in the publications of G. Ramsay, Nature Biotechnology, 1998, n°16, p. 40-44; F. Ginot, Human Mutation, 1997, n°10, p. 1-10; J. Cheng et al, Molecular diagnosis, 1996, n°1(3), p. 183-200; T. Livache et al, Nucleic Acids Research, 1994, n° 22(15), p. 2915-2921; J. Cheng et al, Nature Biotechnology, 1998, n° 16, p. 541-546 or in the U.S. Pat. No. 4,981,783, U.S. Pat. No. 5,700,637, U.S. Pat. No. 5,445,934, U.S. Pat. No. 5,744,305 et U.S. Pat. No. 5,807,522. The main characteristic of the solid support is to keep the hybridization characteristics of the capture probes on the target nucleotide fragments while generating minimum background noise for the detection method.

For immobilizing the probes onto the support, three main types of fabrication can be distinguished.

First, a first technique consists of a deposition of pre-synthesized probes. The probes are attached by direct transfer, by means of micropipettes, of micropoints, or by means of an ink-jet device. This technique makes it possible to fasten probes whose sizes range from a few bases (5 to 10) up to relatively large sizes, from 60 bases (impression) to several hundred bases (micro-deposition).

The impression is an adaptation of the process used by inkjet printers. It is based on the propulsion of very small spheres of fluid (volume<1 nl) and on a pace which can reach 4,000 drops/seconds. The impression involves no contact between the system releasing the fluid and the surface onto which it is deposited.

The micro-deposit consists in attaching probes whose length ranges from a few dozens to several hundred bases at the surface of a glass slide. These probes are generally taken from databases and are in the form of amplified and purified products. This technique makes it possible to make chips called microarrays carrying about ten thousand spots, called recognition areas, of DNA on a surface of a little less than 4 $cm^2$. Not to be forgotten, however, is the use of Nylon membranes, called "microarrays", which carry amplified products, generally by PCR, with a diameter of 0.5 to 1 mm and whose maximum density is 25 spots/$cm^2$. This technique, very flexible, is used by many laboratories. In embodiments of the invention, the latter technique is considered as being part of microchips. One may, however, deposit at the bottom of a microtiter plate, a certain volume of sample in each well, as is the case in patent applications WO-A-00/71750 and FR00/14896, or deposit at the bottom of a same Petri dish, a certain number of drops, separated from one another according to another patent application: FR00/14691.

The second technique for attaching probes onto the support or chip is called the in situ synthesis. This technique leads to the creation of short probes, directly at the surface of the chip. It is based on the synthesis of in situ oligonucleotides (see, in particular, patent applications WO 89/10977 and WO 90/03382) and on the process of oligonucleotide synthesizers. It consists in displacing a reaction chamber where the elongation reaction of oligonucleotides takes place, along the glass surface.

Finally, the third technique is called photolithography, which is a process at the origin of the biochips developed by Affymetrix. It also relates to a synthesis in situ. Photolithography is derived from the techniques of microprocessors. The surface of the chip is modified by attachment of photolabile chemical groups that may be activated by light. Once illuminated, these groups are capable of reacting with the end 3' of an oligonucleotide. By protecting this surface by masks of defined shapes, areas of the chip where one or the other of the four nucleotides are desired to be bound can be illuminated, and thus selectively activated. The successive use of different masks makes it possible to alternate cycles of protection/reaction and therefore to carry out the oligonucleotide probes onto spots of about several dozen square micrometers ($\mu m^2$). This resolution makes it possible to create up to several hundred thousand spots on a surface of a few square centimeters ($cm^2$). Photolithography has several advantages: massively parallel, it enables a chip of N-mers in only 4×N cycles to be created. All these techniques may be used in embodiments of the present invention. According to a preferred embodiment of the invention, the at least one specific reagent of step b), previously defined, comprises at least one hybridization probe, which is preferably immobilized onto a support. This support is preferably a low, high, or average density support such as defined above.

These steps of hybridization onto support comprising a multitude of probes may be preceded by a step of enzymatic amplification reaction, such as defined below, to increase the quantity of target genetic material.

An "amplification primer" is a nucleotide fragment comprising 5 to 100 nucleotides, preferably from 15 to 30 nucleotides, for initiating an enzymatic polymerization, such as, in particular, an enzymatic amplification reaction.

By "enzymatic amplification reaction", one means a process generating multiple copies of a nucleotide fragment through the action of at least one enzyme. Such amplification reactions are well known to one having ordinary skill in the art, and mention may, in particular, be made of the following techniques:
  PCR (Polymerase Chain Reaction), as described in U.S. Pat. No. 4,683,195, U.S. Pat. No. 4,683,202, and U.S. Pat. No. 4,800,159,
  LCR (Ligase Chain Reaction), described, for example, in patent application EP 0 201 184,
  RCR (Repair Chain Reaction), described in patent application WO 90/01069,
  3SR (Self Sustained Sequence Replication) with patent application WO 90/06995,
  NASBA (Nucleic Acid Sequence-Based Amplification) with patent application WO 91/02818, and
  TMA (Transcription Mediated Amplification) with U.S. Pat. No. 5,399,491.

When the enzymatic amplification is a PCR, the specific reagent comprises at least 2 amplification primers, specific for a target gene, so as to make it possible to amplify the material specific for the target gene. The material specific for the target gene then preferably comprises a complementary DNA obtained by reverse transcription of messenger RNA derived from the target gene (reference is then made to target-gene-specific cDNA) or a complementary RNA obtained by transcription of the target-gene-specific cDNAs (reference is then made to target-gene-specific cRNA). When the enzymatic amplification is a PCR carried out after a reverse transcription reaction, this is then called an RT-PCR.

In general, the expression of a target gene may be analyzed by the detection of mRNAs (messenger RNAs) which are transcribed from the target gene at a given time or by the detection of proteins derived from these mRNAs.

The determination of the expression of a target gene by the detection of mRNAs derived from this target gene is carried out by protocols well-known to one having ordinary skill in the art. When the specific reagent comprises at least one amplification primer, the expression of a target gene may be determined in the following manner:

1) after having extracted, as biological material, the total RNAs (comprising the transfer RNAs (tRNAs), the ribosomal RNAs (rRNAs) and the messenger RNAs (mRNAs) from a biological sample, a reverse transcription step is carried out in order to obtain the complementary DNAs (or cDNA) of said mRNAs. By way of example, this reaction of reverse transcription can be carried out using a reverse transcriptase enzyme which makes it possible to obtain, from an RNA fragment, a complementary DNA fragment. The reverse transcriptase enzyme from AMV (Avian Myoblastosis Virus) or from MMLV (Moloney Murine Leukaemia Virus) can, in particular, be used. When it is more particularly desired to obtain only the cDNAs of the mRNAs, this reverse transcription step is carried out in the presence of nucleotide fragments comprising only thymine bases (polyT), which hybridize by complementarity to the polyA sequence of the mRNAs so as to form a polyT-polyA complex which then serves as a starting point for the reverse transcription reaction carried out by the reverse transcriptase enzyme. cDNAs complementary to the mRNAs derived from a target gene (target-gene-specific cDNA) and cDNAs complementary to the mRNAs derived from genes other than the target gene (cDNAs not specific for the target gene) are then obtained;

2) the amplification primer(s) specific for a target gene is (are) brought into contact with the target-gene-specific cDNAs and the cDNAs not specific for the target gene. The amplification primer(s) specific for a target gene hybridize(s) with the target-gene-specific cDNAs and a predetermined region, of known length, of the cDNAs originating from the mRNAs derived from the target gene is specifically amplified. The cDNAs not specific for the target gene are not amplified, and a large amount of target-gene-specific cDNAs is then obtained. Reference is thus made, without distinction, to "target-gene-specific cDNAs" or to "cDNAs originating from the mRNAs derived from the target gene". This step can be carried out in particular by means of a PCR-type amplification reaction or by any other amplification technique as defined above. In PCR, several different cDNAs may be amplified simultaneously, each being specific for different target genes, using several different pairs of amplification primers, each being specific for a target gene: reference is then made to a multiplex amplification.

3) the expression of the target gene is determined by detecting and quantifying the target-gene-specific cDNAs obtained in step 2) above. This detection can be carried out after electrophoretic migration of the target-gene-specific cDNAs according to their size. The gel and the medium for the migration can include ethidium bromide so as to allow direct detection of the target-gene-specific cDNAs when the gel is placed, after a given migration period, on a UV (ultraviolet)-ray light table, through the emission of a light signal. The greater the amount of target-gene-specific cDNAs, the brighter this light signal. These electrophoresis techniques are well known to those skilled in the art. The target-gene-specific cDNAs can also be detected and quantified using a quantification range obtained by means of an amplification reaction carried out until saturation. In order to take into account the variability in enzymatic efficiency that may be observed during the various steps (reverse transcription, PCR, etc.), the expression of a target gene of various groups of patients can be normalized by simultaneously determining the expression of a "housekeeping" gene, the expression of which is similar in the various groups of patients. By realizing a ratio between the expression of the target gene and the expression of the housekeeping gene, i.e. by realizing a ratio between the amount of target-gene-specific cDNAs and the amount of housekeeping-gene-specific cDNAs, any variability between the various experiments is thus corrected. One having ordinary skill in the art can refer, in particular, to the following publications: Bustin S A, *J. Mol. Endocrinol.,* 2002, 29:23-39; Giulietti A. *Methods,* 2001, 25: 386-401.

When the specific reagent comprises at least one hybridization probe, the expression of a target gene may be determined in the following manner:

1) After having extracted, as biological material, the total RNAs from a biological sample as presented above, a reverse transcription step is carried out as described above in order to obtain cDNAs complementary to the mRNAs derived from a target gene (target-gene-specific cDNA) and cDNAs complementary to the mRNAs derived from genes other than the target gene (cDNA not specific for the target gene);

2) All the cDNAs are brought into contact with a support, on which are immobilized capture probes specific for the target gene whose expression it is desired to analyze, in order to carry out a hybridization reaction between the target-gene-specific cDNAs and the capture probes, the cDNAs not specific for the target gene not hybridizing to the capture probes. The hybridization reaction can be carried out on a solid support which includes all the materials as indicated above. According to a preferred embodiment, the hybridization probe is immobilized on a support. Preferably, the support is a low, high, or average density support such as previously defined. The hybridization reaction may be preceded by a step consisting of enzymatic amplification of the target-gene-specific cDNAs as described above, so as to obtain a large amount of target-gene-specific cDNAs and to increase the probability of a target-gene-specific cDNA hybridizing to a capture probe specific for the target gene. The hybridization reaction may also be preceded by a step consisting in labeling and/or cleaving the target-gene-specific cDNAs as described above, for example using a labeled deoxyribonucleotide triphosphate for the amplification reaction. The cleavage can be carried out in particular by the action of imidazole and manganese chloride. The target-gene-specific cDNA can also be labeled after the amplification step, for example by hybridizing a labeled probe according to the sandwich hybridization technique described in document WO-A-91/19812. Other preferred particular embodiments for labeling and/or cleaving nucleic acids are described in patent applications WO 99/65926, WO 01/44507, WO 01/44506, WO 02/090584, WO 02/090319;

3) A step for detecting the hybridization reaction is subsequently carried out. The detection can be carried out by bringing the support on which the capture probes specific for the target gene are hybridized with the target-gene-specific cDNAs into contact with a probe referred to as "detection probe", labeled by a label and detecting the signal emitted by the label. When the target-gene-specific cDNA has been labeled beforehand with a label, the signal emitted by the label is detected directly.

The expression of a target gene can also be detected in the following manner:

1) After having extracted, as biological material, the total RNAs from a biological sample as previously presented, a reverse transcription step is carried out as described above in order to obtain the cDNAs of the mRNAs of the biological material. The polymerization of the complementary RNA of the cDNA is subsequently carried out using a T7 polymerase enzyme which functions under the control of a promoter and which makes it possible to obtain, from a DNA template, the complementary RNA. The cRNAs of the cDNAs of the mRNAs specific for the target gene (reference is then made to target-gene-specific cRNA) and the cRNAs of the cDNAs of the mRNAs not specific for the target gene are then obtained.

2) All the cRNAs are brought into contact with a support on which are immobilized capture probes specific for the target gene whose expression it is desired to analyze, in order to carry out a hybridization reaction between the target-gene-specific cRNAs and the capture probes, the cRNAs not specific for the target gene not hybridizing on the capture probes. When it is desired to analyse simultaneously the expression of several target genes, several different capture probes, each being for a target gene, can be immobilized on the support. The hybridization reaction may also be preceded by a step consisting of labeling and/or cleaving of the target-gene-specific cRNAs as described above.

3) A step consisting in detecting the hybridization reaction is subsequently carried out. The detection can be carried out by brining the support on which the capture probes specific for the target gene are hybridized with the target-gene-specific cRNA into contact with a "detection probe" labeled with a label, and detecting the signal emitted by the label. When the target-gene-specific cRNA has been labeled beforehand with a label, the signal emitted by the label is detected directly. The use of cRNA is particularly advantageous when a biochip-type support on which a large number of probes are hybridized is used.

This preferred method can in particular be carried out by "real time NASBA", which combines, in a single step, the NASBA amplification technique and real-time detection which uses "molecular beacons". The NASBA reaction takes place in the tube, producing the single-stranded RNA with which the specific "molecular beacons" can simultaneously hybridize to give a fluorescent signal. The formation of the new RNA molecules is measured in real time by continuous verification of the signal in a fluorescent reader. Contrary to an amplification using RT-PCR, the NASBA amplification can be carried out in the presence of DNA in the sample. Therefore, it is not necessary to verify that the DNA has effectively been completely eliminated during the RNAs extraction.

The expression of a gene can also be determined by sequencing.

When the biological material comprises proteins, they can be detected by binding partners, for example receptors, antibodies, fragments of antibodies, and any other ligand capable of binding to a protein.

The binding-partner antibodies are, for example, either polyclonal antibodies, or monoclonal antibodies.

The polyclonal antibodies can be obtained by immunization of an animal with the suitable immunogen, followed by recovery of the researched antibodies in purified form, by collecting the serum of said animal, and separating said antibodies from the other serum constituents, in particular by affinity chromatography on a column to which an antigen specifically recognized by the antibodies is attached.

The monoclonal antibodies can be obtained by the hybridoma technique, the general principle of which is outlined hereinafter.

First, an animal, generally a mouse having the suitable immunogen, is immunized, and the B lymphocytes of this animal are capable of producing antibodies against said antigen. These antibody-producing lymphocytes are subsequently fused with "immortal" myeloma cells (murines in the example) so as to produce hybridomas. The heterogeneous mixture of the cells thus obtained is then used to form a selection of the cells capable of producing a particular antibody and of multiplying indefinitely. Each hybridoma is multiplied in the form of a clone, each one resulting in the production of a monoclonal antibody whose recognition properties vis-à-vis the protein can be tested, for example, with an ELISA test, a one- or two-dimensional immunotransfer (Western blot), immunofluorescence, or by means of a biosensor. The monoclonal antibodies thus selected are subsequently purified, in particular according to the affinity chromatography technique described above.

The monoclonal antibodies may also be recombinant antibodies obtained by genetic engineering, using techniques well known to one having ordinary skill in the art.

The binding partners specific for the protein(s) or not of the [X] researched in the process of an embodiment of the invention can be used as capture reagent, detection reagent, or both capture and detection reagent.

The visualization of immune reactions, that is, of the protein/binding partner bond, can be carried out by any detection means such as direct or indirect means.

In the case of direct detection, that is, without the intermediary of labeling, immune reactions are observed, for example using surface plasmon resonance or cyclic voltammetry on an electrode having a conducting polymer.

The indirect detection is carried out by labeling the binding partner.

The term "labeling of binding partners" is intended to mean the attachment of a label capable of directly or indirectly generating a detectable signal. A non-limiting list of these labeling reagents consists of:
- enzymes which produce a signal that is detectable, for example, by colorimetry, fluorescence, or luminescence, such as horseradish peroxidase, alkaline phosphatase, β-galactosidase, glucose-6-phosphate dehydrogenase;
- chromophores, such as fluorescent, luminescent or dye compounds;
- fluorescent molecules, such as Alexa or phycocyanins;
- radioactive molecules, such as $^{32}P$, $^{35}S$, or $^{125}I$.

Indirect detection systems can also be used, such as, for example, ligands capable of reacting with an anti-ligand. The ligand/anti-ligand pairs are well known to one having ordinary skill in the art, which is the case, for example, of the following pairs: biotin/streptavidin, hapten/antibody, antigen/antibody, peptide/antibody, sugar/lectin. In this case, it is the ligand which carries the binding partner. The anti-ligand may be detectable directly via the labeling reagents described in the preceding paragraph, or may itself be detectable via a ligand/anti-ligand.

These indirect detection systems may lead, under certain conditions, to an amplification of the signal. This signal amplification technique is well known to one having ordinary skill in the art, and reference can be made to prior patent applications of the applicant FR98/10084 or WO-A-95/08000.

Depending on the type of labeling used, one having ordinary skill in the art may add reagents for visualizing the labeling.

By way of example of immunological tests as defined above, mention may be made of "sandwich" methods such as ELISA, IRMA, and RIA, "competition" methods, Western-blotting and Dot-blotting.

Flow cytometry and mass spectrometry may also be used for detecting, in a biological fluid, the protein or proteins being researched. The principles of flow cytometry and of mass spectrometry are widely known to one having ordinary skill in the art. By way of example, in mass spectrometry, a biological sample, pretreated or not, is passed through a mass spectrometer and the spectrum obtained is compared to a reference spectrum. An example of pretreatment of the sample consists in passing it over an immunocapture support comprising one of the binding partners of the researched protein(s). Another example of pretreatment of the sample may be pre-fractionation of the biological sample in order to separate the proteins of the sample from one another. In techniques well known to one having ordinary skill in the art, the predominant proteins of the sample may, for example, first of all be depleted.

Figure 1:
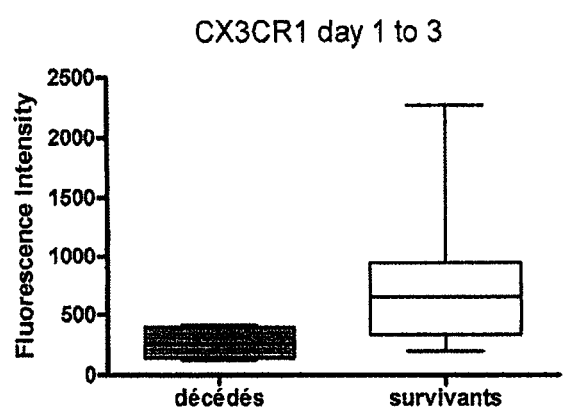
FIG. 1 shows the expression of CX3CR1 (mRNA) measured by microarray. The measurement is given in fluorescence intensity. D0 corresponding to the day of the accident, collection from the patients were made between day 1 and day 3. A significant diminution of the CX3CR1 expression was noticed for deceased patients (dark grey) with respect to that of surviving patients (white)

Example: Search for an expression profile for the survival prognosis of a major burn victim.

EXAMPLES

Characteristics of the Biological Samples

1. Group of Patients:

The study was carried out on 24 major burn victims from 19-years old to 75-years old (17 men, 7 women, median age: 46-years old) admitted into the intensive care unit for major burn victims, building I of the Hospital Edouard Herriot-Lyon (France) between 2004 and 2009 for treatment of a burn whose surface, burned to the $2^{nd}$ or $3^{rd}$ degree, is greater than or equal to 30% of the body surface. The severity of the infliction is calculated using the ABSI (Abbreviated Burn Severity Index) score established by Tobiasen and which takes into account the sex, the age, the surface area, the depth of the lesions and the possible impairment of the lungs. This score is inversely proportional to the survival, which is at 50% and 20% for a score of 8 and 10, respectively (Tobiasen et al., Ann. Emerg. Med., 1982. 11(5): p. 260-2). For the group of patients studied, the median ABSI score is 11.5 and the median surface burned is 70%. The patients are all heavily sedated and on mechanical ventilation because of the extent and/or location of the burns. The initial resuscitation is carried out using a filling calculated according to the Parkland (Baxter) formula. The vascular filling is monitored. The enteral nutrition is quickly set up and progressively increased. The bandages are made with FLAMMAZINE®. The surgical treatment, with excision and graft, are started quickly, as early as the first week, then continue at a pace of once to twice a week. These patients are all in a state of shock, necessitating a treatment with amines after vascular filling.

Patients younger than 18-years old as well as patients presenting a pregnancy, a polytraumatism, a right or left vascular dysfunction, an evolutive cancer, in a septic shock suspected during the initial clinical examination, were excluded.

2. Control Series

Healthy volunteers were recruited so as to obtain a control series whose samples were treated and analyzed under conditions identical to those of the sick patients. They were recruited among the patients of the Plastic Surgery department of the hospital Edouard Herriot and among the personnel of the medical team. They were healthy people (4 women and 1 man) whose median age was 39-years old, without any toxic habit, particularly smoking, and undergoing no medical treatment. Their physical examination revealed nothing particular, their full blood count and CRP assay were normal.

3. Sampling and Data Collection

The first blood samples are obtained at the latest 72 hours after the beginning of the burn and then, blood is collected from each patient every 48 hours during 8 days. Taking into consideration the beginning of the burn as D0, each patient was monitored for a period of 11 days maximum. On the basis of the mortality observed during this period, 8 patients died during their hospitalization at the intensive care unit. Six patients died prematurely during the first 10 days after the burn. In all the cases, the patients presented a picture of multivisceral failure. In 5 cases, a septicemia-type of infectious complication was observed. Thirteen patients developed an infection documented within the first 10 days. Eleven patients developed secondary septic shock (after the study period) during their hospitalization. Two patients died secondarily of this complication. The clinical data of the burned patients included in the study are presented in table 1.

TABLE 1 clinical data for burned patients included in the study

| | 1/GRA | 2/PL4 | 3/URB | 4/LEF | 5/LCU | 6/PI2 | 7/EEY | 8/CCU | 9/DEP | 10/SER | 11/ATT | 12/5AI |
|---|---|---|---|---|---|---|---|---|---|---|---|---|
| sexe masculin | X | X | X | X | X | X | | | | | | X |
| sexe féminine | | | | | | | X | X | X | X | X | |
| âge | 52 | 40 | 43 | 36 | 42 | 45 | 75 | 56 | 50 | 63 | 45 | 34 |
| score ABSI | 23 | 11 | 12 | 22 | 13 | 24 | 22 | 9 | 10 | 11 | 5 | 9 |
| perfusion de plasma frais | | | | | | X | | | | | | |
| transfusion avant inclusion | | | | X | | X | | | | | | |
| incision de décharge | | | | | X | X | | | | | | X |
| transfusion sanguine ou PFC | | | | | | X | | | | | | |
| J1 | | | | | | | | | | | | |
| J2 | | | | X | | | | | | | | |
| J3 | X | X | X | | X | X | X | X | X | X | X | X |
| délai heure début/inclusion (h) | 57 | 53 | 41 | 43 | 70 | 62 | 51 | 71 | 35 | 47 | 64 | 61 |
| inclusion précoce P/tardive T | | | | | T | | | T | P | | | |
| débit de noradrénaline >1 μg/kg/min | | | X | | X | | X | | | | | |
| cortisolémie initiale | 214 | 422 | 234 | 122 | 380 | 205 | 287 | 553 | 423 | 503 | 274 | 403 |
| taux max cu cortisol < | 225 | 525 | 571 | 367 | 437 | 525 | 529 | 925 | 599 | 549 | 642 | 805 |
| IL6 | | | | | | 2888 | | 2883 | | | | |
| absence de réponse au test du syancthène | X | X | X | X | X | X | X | | X | X | | |
| infection précoce <10j | | X | X | X | | X | X | X | | | | X |
| infection nosocomiale précoce | | X | X | X | | X | X | | | | | X |
| data à 1ere infection | | J5F | J4P | J5P+U | | J4J | J5P | J1P | | | | J4P |
| infection pulmonaire précoce | | X | X | X | | X | X | X | | | | X |
| hémoculture positive précoce | | | | | | X | X | | | | | |
| versus | | | | | | | | | | | | |
| infection précoce autre | | | X | | | | | X | X | | | |
| nombre d'infections | | 1 | 2 | 1 | | 4 | 2 | 2 | 1 | 1 | 4 | 3 |
| choc septique secondaire | | | X | | | | X | X | | | X | X |
| CWH | | | | | | | | | | | | |
| cytolyse hépatique et IHC | | | | | | | | | | | | |
| SDRA | | | X | X | | | | X | | | | X |
| TIH | | | X | X | | | | X | | | | |
| décès par défaillance multiviscérale | X | | | | | | | | | | | |
| Décès précoce <10j | X | | | | | | | | | | | |
| versus | | | | | | X | | | | | X | X |

| | 13/FOL | 14/GUE | 15/OUT | 16/PLA | 17/ARY | 18/C-C | 19/BCN | 20/CHA | 21/EL3 | 22/3A1/ | 23/PO | 24/EFL |
|---|---|---|---|---|---|---|---|---|---|---|---|---|
| sexe masculin | X | | | X | X | X | X | X | X | X | X | X |
| sexe féminine | | X | X | | | | | | | | | |
| âge | 48 | 48 | 66 | 32 | 38 | 35 | 58 | 42 | 35 | 46 | 43 | 19 |
| score ABSI | 13 | 13 | 5 | 11 | 10 | 15 | 12 | 10 | 12 | 13 | 11 | 12 |
| perfusion de plasma frais | X | | | | | | X | X | | | | X |
| transfusion avant inclusion | X | | | | | | X | | | | | X |
| incision de décharge | X | | | X | | X | X | | X | | | X |

TABLE 1-continued

| | | | | | | | | | | | | |
|---|---|---|---|---|---|---|---|---|---|---|---|---|
| transfusion sanguine ou PFC | X | X | | | | | | | | | X | X |
| J1 | X | | | | | | | X | | | | |
| J2 | X | | | | | | | | | | | |
| J3 | | | | | X | | | | | | | |
| délai heure début/inclusion (h) | 21 | 64 | 58 | 45 | 21 | 72 | 46 | 62 | 39 | 56 | 24 | 24 |
| inclusion précoce P/tardive T | | T | | | P | T | | | | | P | F |
| débit de noradrénaline >1 µg/kg/min | | | | | | | X | | | | | |
| cortisolémie initiale | 634 | 275 | 307 | 223 | 231 | 422 | 1222 | 336 | 183 | 202 | 156 | 285 |
| taux max cu cortisol < | 1136 | 730 | 567 | 552 | 367 | 920 | 1510 | 1306 | 444 | 577 | 291 | 413 |
| IL6 | 376 | 2087 | | 450 | 615 | 4420 | 8200 | 3264 | 1517 | | | |
| absence de réponse au test du syancthène | | | X | | X | | | | X | | X | X |
| infection précoce <10j | X | X | X | | X | X | | X | X | X | X | |
| infection nosocomiale précoce | X | X | X | | X | X | | X | X | X | X | |
| data de a 1ere infection | J5S | | J5P4S | J12P | J11P | J5P3 | J43 | JEF | J7P | J4F | | |
| infection pulmonaire précoce | | | X | | X | X | | X | X | X | | |
| hémoculture positive précoce | | | X | | X | X | | | X | | | |
| versus | | X | | | | | X | | | | | |
| infection précoce autre | | | | | | | | | | | | |
| nombre d'infections | 1 | 3 | 3 | 2 | 5 | | 1 | 4 | 3 | 5 | | |
| choc septique secondaire | | X | | X | X | | | X | X | | | |
| CWH | X | | X | | | X | | X | | | | X |
| cytolyse hépatique et IHC | X | | X | | | X | | X | | | | |
| SDRA | X | | | | | X | | X | | | | |
| TIH | | | | | | | | | | | | |
| décès par défaillance multiviscérale | X | | | | X | X | X | X | | | X | |
| Décès précoce <10j | X | | | | X | X | X | X | | | X | |
| versus | | X | X | X | X | X | X | X | | X | X | |

| French | English |
|---|---|
| sexe masculin | male |
| sexe féminine | female |
| âge | age |
| score ABSI | ABSI score |
| perfusion de plasma frais | perfusion of fresh plasma |
| transfusion avant inclusion | transfusion before inclusion |
| incision de décharge | escharotomy |
| transfusion sanguine ou PFC | blood transfusion or PFC |
| J1 | D1 |
| J2 | D2 |
| J3 | D3 |
| délai heure début/inclusion T | period hour beginning/inclusion (h) |
| inclusion précoce P/tardive T | premature inclusion P/late T |
| débit de noradrenaline >1 µg/kg/min | noradrenaline flow rate >1 µg/kg/min |
| cortisolémie initiale | initial plasma cortisol |
| taux max cortisol < | max cortisol rate < |
| IL6 | IL6 |
| absence de réponse au test du synacthène | lack of response to synacthen test |
| infection précoce <10j | premature infection <10d |
| infection nosocomiale précoce | premature nosocomial infection |
| date de la 1ere infection | date of 1$^{st}$ infection |

TABLE 1-continued

| | |
|---|---|
| infection pulmonaire précoce | premature pulmonary infection |
| hémoculture positive précoce | premature positive blood culture |
| versus | |
| infection précoce autre | other premature infection |
| nombre d'infections | number of infections |
| choc septique secondaire | secondary septic shock |
| CWH | |
| cytolyse hépatique et IHC | hepatic cytolysis and IHC |
| SDRA | ARDS |
| TIH | HIT |
| décès par défaillance multiviscérale | death by multivisceral failure |
| Décès précoce <10j | premature death <10d |
| versus | versus |

Extraction of the Biological Material (Total RNAs) from the Biological Sample

The samples were collected directly into PAXGENE™ BLOOD RNA (PREANALYTIX, Hilden, Germany). After the step of collecting the blood sample, the tubes were left at room temperature for 2 hours, and then kept at −80° C. until the extraction of the biological material for the purpose of optimizing and standardizing the preservation of the samples. More precisely, in this protocol, the total RNAs were extracted using PAXGENE™ BLOOD RNA® (PREANALYTIX) kits while complying with the manufacturer's recommendations.

Briefly, the tubes were centrifuged (no need to have this level of detail I think) in order to obtain a pellet of nucleic acids. This pellet was washed and resuspended in a proteinase k buffer necessary to the digestion of proteins. A new centrifugation was carried out to eliminate cell debris and ethanol was added in order to optimize the binding conditions of nucleic acids. The total RNAs were specifically bound to the Paxgene RNA spin columns and, before the elution of the latter, the contaminating DNA was digested using an RNAsefree DNAse set (Qiagen Ltd, Crawley, UK). The quality of the total RNAs was analyzed using the bioanalyzer AGILENT 2100 (Agilent Technologies, Waldbronn, Germany) by means of the Lab-on-chip RNA 6000 Nano Assay system (Agilent). The total RNAs comprise the transfer RNAs, the messenger RNAs (mRNA) and the ribosomal RNAs.

Measurement of the CX3CR1 (mRNA) Expression by Microarray

The reverse transcription reaction of mRNAs is carried out using the Affymetrix protocol from 3 µg of the total RNA. A polyT oligonucleotide primer was used to target only the mRNAs contained in the solution of total RNAs during the reverse transcription. The entirety of the steps was carried out with the AFFYMETRIX-GENECHIP® One-Cycle Target Labeling and Control Reagents kit. The products of the reverse transcription (cDNA) were then used for the synthesis of the biotin-labeled cRNA for 16 hours at 37° C. After the cRNA purification step to remove unincorporated dNTPs, the cRNAs were quantified and fragmented. Monitoring the fragmentation is done by capillary electrophoresis (Agilent). The cRNA hybridization is carried out using the biochip GeneChipHuman Genome U133 Plus 2 before the signal amplification step by incubation with the SAPE mix containing the Streptavidin-Phycoerythrin, then the goat IgG antibodies anti-Streptavidin were mixed with the anti-goat IgG biotinylated antibody. This last step uses the Fluidic FS450 platform. The analysis of Affymetrix data started with the image capture of the biochip by the AFFYMETRIX scanner GENECHIP® 3000. The data are then normalized by RMA (Robust Multiple-Array Average). All the data based on signal intensity are used after normalization. The differences of mRNA expression levels between patients having a good and a poor prognosis are determined by the SAM method.

Among the genes differentially expressed at D1-D3 between the deceased and the surviving patients, CX3CR1 is identified with a high difference of expression as shown in table 2 below and in FIG. 1.

TABLE 2

Measurement of the CX3CR1 (mRNA) expression by microarray among the deceased patients (P. deceased) and the surviving patients (P. surviving). The results are expressed by the median of the Fluorescence intensities

| ID | Gene | P. deceased | P. surviving | Fold change |
|---|---|---|---|---|
| 205898_at | CX3CR1 | 257.16 | 622.17 | 2.42 |

Measurement of the CX3CR1 (mRNA) Expression by Quantitative RT-PCR

In order to confirm the results by means of another technique of molecular biology, the CX3CR1 mRNA expression was measured by quantitative RT-PCR. Briefly, a reverse transcription (RT) reaction is carried out in a final volume of 20 µl. The total RNA (0.5 µg) is mixed with 1 µl of polyT at 50 µm and 1 µl of annealing buffer (SUPERSCRIPT™ III First-Strand Synthesis SuperMix, Invitrogen), then incubated for 5 min. at 65° C. After cooling in ice, the solution was mixed with 10 µl of 2× First-Strand Reaction Mix and 2 µl SuperScript III/RnaseOUT Enzyme Mix, all these products originating from SUPERSCRIPT™ III First-Strand Synthesis SuperMix (Invitrogen). The reverse transcription was carried out for 50 min at 50° C. and then stopped for a 5-minute incubation at 85° C. To finish, each cDNA solution was diluted 1:10 in DEPC water. For each of the genes of interest, a standard was prepared by a PCR (polymerase chain reaction) amplification led up to saturation. The amplicons obtained were purified (PCR purification kit, Qiagen Ltd) and the presence of a single amplicons were verified by fusion curve analysis.

The standard of the peptidylpropyl isomerase B (PPIB) "housekeeping" gene encoding cyclophilin B was obtained from Search-LC (Heidelberg, Germany).

The LIGHTCYCLER™ 2.0 (Roche) was used and the PCR reactions were carried out using the FAST-STAR™ DNA Master SYBR Green I real-time PCR kit (Roche Molecular Biochemicals). Each PCR was carried out in a final volume of 20 µl containing 1 µl of LC-FAST-START Reaction Mix SYBR Green I, 1 µl of LC-FAST-START DNA Master SYBR Green I/Enzyme (including the Taq DNA polymerase, the reaction buffer and a mixture of deoxynucleotide triphosphate), some $MgCl_2$ (3 mM final concentration), the sense and antisense primers (0.5 µM final concentration), and 10 µl of cDNA solution. After a 10-min denaturation step at 95° C., the amplification was carried out by means of 40 cycles of a PCR "touch-down" protocol PCR (10 s at 95° C., 10 s of hybridization at 68-58° C., followed by a 16-s extension at 72° C.). At the end of each cycle, the fluorescence emitted by the SYBR Green was measured.

The combination of primers necessary to the quantification of the housekeeping gene CPB was provided by Search-LC (Heidelberg, Germany; reference 488116). The combination of primers necessary to the quantification of CX3CR1 is described in table 3.

TABLE 3

CX3CR1 primers used for RT-PCR

| Target gene | | Primers |
|---|---|---|
| CX3CR1 | Sense 5'→3' | TGACTGGCAGATCCAGAGGTT (SEQ ID NO. 1) |
| NM_001337.3 | Antisense 3'→5' | GTAGAATATGGACAGGAACAC (SEQ ID NO. 2) |

(SEQ. ID NOS:1 and 2)

The size of the obtained amplicon is 163 bases.

The quantity of target mRNA relative to the quantity of mRNA of the housekeeping gene PPIB was analyzed by means of the relative quantification technique using the LIGHTCYCLER Relative Quantification Software (Roche Molecular Biochemicals). The "Second Derivative Maximum Method" of the LIGHTCYCLER™ software (Roche) was used to determine automatically the Crossing Point (Cp)

for each sample. The Cp value was defined as the number of cycles for which the fluorescence was significantly different from the background noise.

Five dilutions in series at 1:10 were carried out in quadruplicate with each standard in order to generate a calibration curve expressing the Cp as a function of the logarithm of the number of copies. The dilutions of standards were optimized in order for the calibration curve to cover the expected expression level for the target gene and for the housekeeping gene. The relative standard curves showing the effectiveness of PCR for the target gene and for the housekeeping gene were generated and used to carry out quantification with the LIGHTCYCLER Relative Quantification Software (Roche Molecular Biochemicals).

Figure 2:
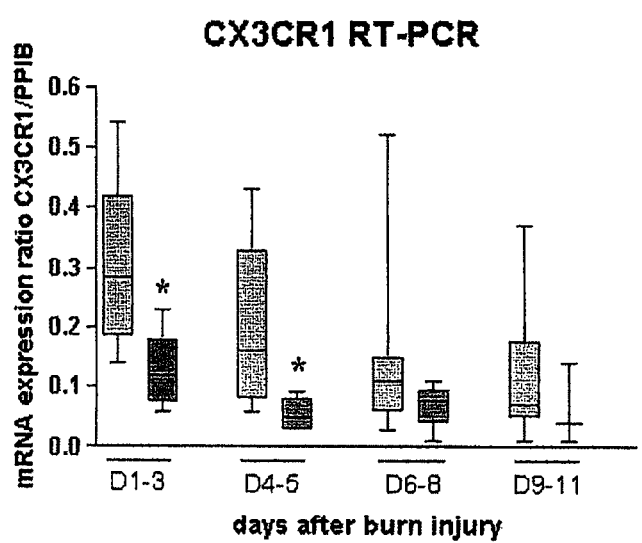
FIG. 2 presents the quantification of CX3CR1 mRNAs in the blood of major burn victims. The box plots represent the distribution of the fluorescence of major burn victims. The gene expression level was measured by quantitative RT-PCR in 24 burn victims (6 deceased patients: dark grey and 18 survivors: light grey) (*$p<0.05$). D signifies the day, D0 being the day of the accident. A significant difference between the two groups was observed at D1-D3 and D4-D5, with a diminution of the expression more significant for patients who decease.

The results obtained for the mRNA CX3CR1 assay by quantitative RT-PCR are presented in FIG. 2. The difference between the surviving and the deceased patients was analyzed by means of the Mann-Whittney test.

A significant difference between the two groups was observed at D1-D3 and D4-D5 with a diminution of the expression more significant for the patients who die.

Correlation of the Results Obtained with the Biochip and by RT-PCR

Figure 3:
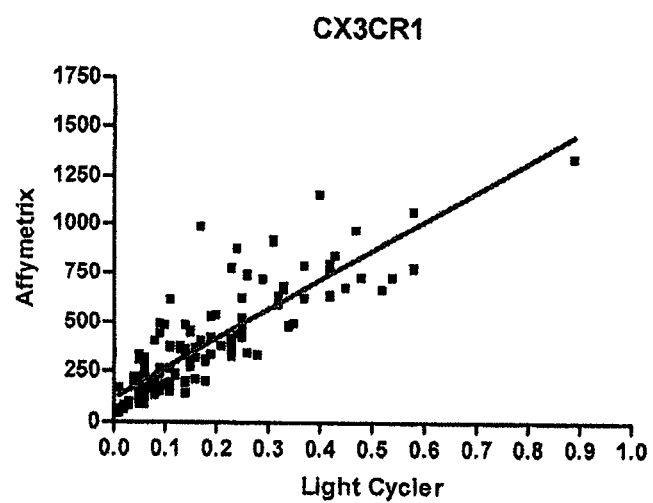
FIG. 3 shows the correlation of the CX3CR1 expression levels between Affymetrix and quantitative RT-PCR. A significant correlation was observed between the Affymetrix results and those obtained by quantitative RT-PCR, confirming the relevance of the CX3CR1 gene.

The correlation of the results obtained, on the one hand with the biochip and, on the other hand, with the quantitative RT-PCR technique was established using the Spearman correlation test (Table 4 and FIG. 3).

TABLE 4

Correlation of the expression levels of CX3CR1 between Affymetrix and quantitative RT-PCR.

| Abbreviated gene name | Affymetrix median BP | Affymetrix median MP | median RT-PCR BP | median RT-PCR MP | Spearman coefficient correlation: r | Spearman test significancy: p |
|---|---|---|---|---|---|---|
| CX3CR1 | 622.17 | 257.16 | 0.285 | 0.12 | 0.86 | P < 0.0001 |

A significant correlation was observed between the Affymetrix results and those of quantitative RT-PCR, confirming the relevance of the CX3CR1 gene.

What is claimed is:

1. An in vitro method of providing a survival prognosis for a patient having SIRS, the method comprising:

measuring expression levels of a combination of target genes from biological material of a sample obtained from the patient using reagents specific for the respective target gene products that are selected from the group consisting of probes, primers, antibodies, and antibody fragments;

comparing the expression levels to one or more predetermined thresholds indicative of a survival prognosis for the patient; and providing a survival prognosis for the patient so that care for the patient is able to be determined in accordance with the survival prognosis, wherein the combination of target genes includes at least one CX3CR1 gene and at least one other target gene selected from the group consisting of S100A8, S100A9, IL-10, TNFA, HLA-DR, CIITA, and IRAK3.

2. The method of claim 1, wherein the patient is a burn victim.

3. The method of claim 2, wherein the sample is collected by the third day after the patient was burned.

4. The method of claim 1, wherein the expression levels are measured using primers specific for at least one target gene product.

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: synthetic construct

<400> SEQUENCE: 1
tgactggcag atccagaggt t                                           21

<210> SEQ ID NO 2
<211> LENGTH: 21
<212> TYPE: DNA
<213> ORGANISM: Artificial Sequence
<220> FEATURE:
<223> OTHER INFORMATION: synthetic construct

<400> SEQUENCE: 2
gtagaatatg gacaggaaca c                                           21

5. The method of claim 4, wherein the primers comprise a first primer that includes the nucleotide sequence of SEQ ID NO:1 and a second primer that includes the nucleotide sequence of SEQ ID NO:2.

6. The method of claim 1, wherein the sample is selected from the group consisting of blood, serum, plasma, saliva, urine, cerebrospinal fluid, pleural fluid, peritoneal fluid, and tissue samples.

7. The method of claim 1, wherein the biological material comprises nucleic acids.

8. The method of claim 1, wherein the biological material comprises proteins.

9. The method of claim 1, wherein the expression levels are measured using at least one probe specific for at least one target gene product.

10. The method of claim 1, wherein the expression levels are measured using at least one antibody or antibody fragment specific for at least one target gene product.

11. A kit for establishing an in vitro prognosis on a patient exhibiting SIRS, the kit comprising:
at least one specific reagent of at least one CX3CR1 gene product;
at least one specific reagent of at least one other target gene product selected from the group consisting of S100A8, S100A9, IL-10, TNFA, HLA-DR, CIITA, and IRAK3 gene products, wherein the kit comprises no more than 12 specific reagents of 12 target gene products; and
instructions describing the predictive value of the expression of said genes to establish a survival prognosis for a SIRS patient,
wherein the specific reagents are selected from the group consisting of nucleic acids covalently attached to a detectable label or a solid support, antibodies, and antibody fragments.

12. The kit of claim 11, wherein the specific reagents comprise at least one detection probe attached to a detectable label that is specific for at least one target gene product.

13. The kit of claim 11, wherein the specific reagents comprise at least one antibody or antibody fragment specific for at least one target gene product.

14. The kit of claim 11, wherein the specific reagents comprise at least one detection or capture probe attached to a detectable label or a solid support that is specific to a CX3CR1 gene product.

15. The kit of claim 11, wherein the specific reagents comprise at least one capture probe attached to a solid support that is specific to a CX3CR1 gene product.

16. The kit of claim 11, wherein the specific reagents comprise at least one detection probe attached to a detectable label that is specific to a CX3CR1 gene product.

17. The kit of claim 11, wherein the specific reagents comprise at least one antibody or antibody fragment specific to a CX3CR1 gene product.

18. The kit of claim 11, comprising specific reagents for at least three target gene products.

19. The kit of claim 11, comprising specific reagents for at least four target gene products.

20. An in vitro kit for providing a survival prognosis for a patient having SIRS, the kit comprising:
at least one reagent specific for at least one CX3CR1 target gene product;
at least one reagent specific for at least one other target gene product selected from the group consisting of S100A8, S100A9, IL-10, TNFA, HLA-DR, CIITA, and IRAK3 gene products; and
instructions that describe how to use the kit to provide a survival prognosis for a patient having SIRS, wherein:
the reagents are selected from the group consisting of nucleic acids covalently attached to a detectable label or a solid support, antibodies, and antibody fragments; and
the kit does not have more than 12 reagents specific for more than 12 target genes.

21. The method of claim 1, wherein the expression levels of no more than 12 target genes are measured.

22. A method comprising measuring expression levels of a combination of target genes from biological material of a sample obtained from a patient having SIRS, wherein the combination of target genes includes at least one CX3CR1 gene and at least one other target gene selected from the group consisting of S100A8, S100A9, IL-10, TNFA, HLA-DR, CIITA, and IRAK3.

23. The method of claim 22, wherein the expression levels of no more than 12 target genes are measured.

24. The method of claim 22, wherein the patient is a burn victim.

25. The method of claim 24, wherein the sample is collected by the third day after the patient was burned.

26. The method of claim 22, wherein the sample is a blood sample.

27. The method of claim 22, wherein the expression levels of the combination of target genes are measured using reagents specific for the respective target gene products that are selected from the group consisting of probes, primers, antibodies, and antibody fragments.

* * * * *